United States Patent [19]

Hormann

[11] Patent Number: 5,482,962

[45] Date of Patent: Jan. 9, 1996

[54] INSECTICIDAL N,N'-DISUBSTITUTED-N-N'-DIACYLHYDRAZINES

[75] Inventor: Robert E. Hormann, Philadelphia, Pa.

[73] Assignee: Rohm and Haas Company, Philadelphia, Pa.

[21] Appl. No.: 279,132

[22] Filed: Jul. 22, 1994

[51] Int. Cl.$^6$ .......................... A01N 43/38; A01N 43/80; A01N 43/74; A01N 43/12; C07D 209/08; C07D 327/04; C07D 261/20; C07D 275/06

[52] U.S. Cl. .......................... 514/415; 548/122; 548/123; 548/126; 548/127; 548/180; 548/207; 548/217; 548/261; 548/241; 548/304.4; 548/361.1; 548/490; 548/503; 549/33; 549/32; 549/53; 549/462; 514/359; 514/360; 514/361; 514/362; 514/364; 514/367; 514/373; 514/375; 514/379; 514/394; 514/403; 514/406; 514/416; 514/439; 514/440; 514/443

[58] Field of Search ..................... 548/490, 503, 548/217; 514/415, 443, 375; 549/53

[56] References Cited

U.S. PATENT DOCUMENTS

| | | | |
|---|---|---|---|
| 4,857,550 | 8/1989 | Kameswaran et al. | 514/522 |
| 5,117,057 | 5/1992 | Hsu et al. | 564/149 |

FOREIGN PATENT DOCUMENTS

| | | | |
|---|---|---|---|
| 4235177 | 8/1992 | Japan . | |
| 0483647 | 10/1991 | United Kingdom . | |

*Primary Examiner*—Johann Richter
*Assistant Examiner*—Laura R. Cross
*Attorney, Agent, or Firm*—Clark R. Carpenter; Thomas D. Rogerson

[57] ABSTRACT

This invention relates to N,N'-disubstituted-N,N'-diacylhydrazines which are useful as insecticides, compositions containing those compounds and methods of their use. This invention also relates to the production of intermediates useful in the production of such compounds.

The compounds of this invention may be represented by the formula

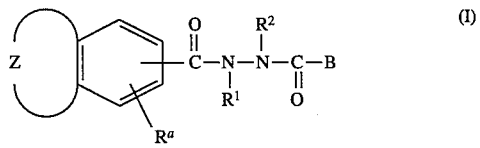

wherein
$R^1$ is cyano or H,
$R^2$ is branched alkyl,
B is aryl or substituted aryl,
$R^a$ is H or a variety of substituents, and
Z forms a fused 5-member heterocyclic ring.

9 Claims, No Drawings

INSECTICIDAL N,N'-DISUBSTITUTED-N-N'-DIACYLHYDRAZINES

BACKGROUND OF THE INVENTION

This invention relates to N,N'-disubstituted-N,N'-diacylhydrazines which are useful as insecticides, compositions containing those compounds and methods of their use. This invention also relates to the production of intermediates useful in the production of such compounds.

The search for compounds which have a combination of excellent insecticidal activity and low undesirable toxicity is a continuing one because of factors such as the desire for compounds exhibiting greater activity, better selectivity, lower undesirable environmental impact, lower production and market cost and higher effectiveness against insects which are or become resistant to many known insecticides.

There continues to be a need to develop insecticidal compounds having improved insecticidal and methods of production properties as described above. The present invention provides improved N,N'-disubstituted-N,N'-diacylhydrazines which are unexpectedly propertied with enhanced, higher activity. The combination of higher activity and lower undesirable toxicity can provide an economic and environmental advantage in the use of the inventive compounds. Compounds of the present invention are particularly suitable for controlling plant-destructive insects in crops of cultivated plants, ornamentals and forestry.

U.S. Pat. No. 5,117,057 discloses insecticidal N'-substituted-N,N'-disubstituted hydrazines and Japanese Kokai Hei 4-235177 discloses new hydrazine derivatives and their use as the effective ingredient in insecticide compositions.

SUMMARY OF THE INVENTION

In accordance with the present invention, there are provided insecticidal compounds having the formula

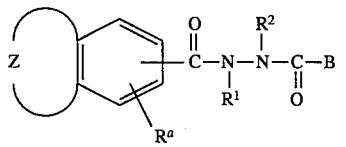

wherein
$R^1$ is cyano or a hydrogen atom (H);
$R^2$ is a branched ($C_3$–$C_{10}$)alkyl or a ($C_1$–$C_4$) straight chain alkyl substituted with one or two of the same or different ($C_3$–$C_6$)cycloalkyl;
B is phenyl, naphthyl, or phenyl or naphthyl substituted with one to three of the same or different substituents selected from the group consisting of halo, cyano, nitro, hydroxy, mercapto, thiocyanato, ($C_1$–$C_4$)alkyl, ($C_1$–$C_4$)alkoxy, halo($C_1$–$C_2$)alkyl, halo($C_1$–$C_2$)alkoxy, ($C_1$–$C_4$)alkylthio, ($C_1$–$C_4$)alkylsulfinyl, ($C_1$–$C_4$)alkylsulfonyl, carboxy, formyl, ($C_1$–$C_4$)alkylcarbonyl, ($C_1$–$C_4$)alkoxycarbonyl, ($C_1$–$C_4$)alkanoyloxy, amino, ($C_1$–$C_4$)alkylamino, di($C_1$–$C_4$)alkylamino having independently the stated number of carbon atoms in each alkyl group, carbamoyl, ($C_1$–$C_4$)alkylcarbamoyl, di($C_1$–$C_4$)alkylcarbamoyl having independently the stated number of carbon atoms in each alkyl group, cyano($C_1$–$C_4$)alkyl, ($C_1$–$C_4$)alkoxy($C_1$–$C_4$)alkyl, ($C_2$–$C_6$)alkenyl, ($C_4$–$C_6$)alkadienyl, ($C_2$–$C_6$)alkynyl, ($C_1$–$C_4$)alkyldithionate, ($C_1$–$C_4$)alkylcarbonylthio, tri($C_1$–$C_4$)alkylsilyl having independently the stated number of carbon atoms in each alkyl group, phenyl, phenyl substituted with one to two of the same or different substituents selected from the group consisting of halo, cyano, nitro, hydroxy, ($C_1$–$C_4$)alkyl, ($C_1$–$C_4$)alkoxy, halo($C_1$–$C_2$)alkyl, halo($C_1$–$C_2$)alkoxy, ($C_1$–$C_4$)alkylthio, ($C_1$–$C_4$)alkylsulfinyl, ($C_1$–$C_4$)alkylsulfonyl, carboxy, formyl, ($C_1$–$C_4$)alkylcarbonyl, ($C_1$–$C_4$)alkoxycarbonyl, ($C_1$–$C_4$)alkanoyloxy, amino, ($C_1$–$C_4$)alkylamino, di($C_1$–$C_4$)alkylamino having independently the stated number of carbon atoms in each alkyl group, phenoxy, phenoxy substituted with one to two of the same or different substituents selected from the group consisting of halo, cyano, nitro, hydroxy, ($C_1$–$C_4$)alkyl, ($C_1$–$C_4$)alkoxy, halo($C_1$–$C_2$)alkyl, halo($C_1$–$C_2$)alkoxy, ($C_1$–$C_4$)alkylthio, ($C_1$–$C_4$)alkylsulfinyl, ($C_1$–$C_4$)alkylsulfonyl, carboxy, formyl, ($C_1$–$C_4$)alkylcarbonyl, ($C_1$–$C_4$)alkoxycarbonyl, ($C_1$–$C_4$)alkanoyloxy, amino, ($C_1$–$C_4$)alkylamino, di($C_1$–$C_4$)alkylamino having independently the stated number of carbon atoms in each alkyl group, benzoyl, benzoyl substituted with one to two of the same or different substituents selected from the group consisting of halo, cyano, nitro, hydroxy, ($C_1$–$C_4$)alkyl, ($C_1$–$C_4$)alkoxy, halo($C_1$–$C_2$)alkyl, halo($C_1$–$C_2$)alkoxy, ($C_1$–$C_4$)alkylthio, ($C_1$–$C_4$)alkylsulfinyl, ($C_1$–$C_4$)alkylsulfonyl, carboxy, formyl, ($C_1$–$C_4$)alkylcarbonyl, ($C_1$–$C_4$)alkoxycarbonyl, ($C_1$–$C_4$)alkanoyloxy, amino, ($C_1$–$C_4$)alkylamino, di($C_1$–$C_4$)alkylamino having independently the stated number of carbon atoms in each alkyl group, phenoxycarbonyl, phenoxycarbonyl substituted with one to two of the same or different substituents selected from the group consisting of halo, cyano, nitro, hydroxy, ($C_1$–$C_4$)alkyl, ($C_1$–$C_4$)alkoxy, halo($C_1$–$C_2$)alkyl, halo($C_1$–$C_2$)alkoxy, ($C_1$–$C_4$)alkylthio, ($C_1$–$C_4$)alkylsulfinyl, ($C_1$–$C_4$)alkylsulfonyl, carboxy, formyl, ($C_1$–$C_4$)alkylcarbonyl, ($C_1$–$C_4$)alkoxycarbonyl, ($C_1$–$C_4$)alkanoyloxy, amino, ($C_1$–$C_4$)alkylamino, di($C_1$–$C_4$)alkylamino having independently the stated number of carbon atoms in each alkyl group, phenylthio, phenylthio substituted with one to two of the same or different substituents selected from the group consisting of halo, cyano, nitro, hydroxy, ($C_1$–$C_4$)alkyl, ($C_1$–$C_4$)alkoxy, halo($C_1$–$C_2$)alkyl, halo($C_1$–$C_2$)alkoxy, ($C_1$–$C_4$)alkylthio, ($C_1$–$C_4$)alkylsulfinyl, ($C_1$–$C_4$)alkylsulfonyl, carboxy, formyl, ($C_1$–$C_4$)alkylcarbonyl, ($C_1$–$C_4$)alkoxycarbonyl, ($C_1$–$C_4$)alkanoyloxy, amino, ($C_1$–$C_4$)alkylamino, di($C_1$–$C_4$)alkylamino having independently the stated number of carbon atoms in each alkyl group, phenyl($C_1$–$C_4$)alkyl, phenyl($C_1$–$C_4$)alkyl substituted on the phenyl ring with one to two of the same or different substituents selected from the group consisting of halo, cyano, nitro, hydroxy, ($C_1$–$C_4$)alkyl, ($C_1$–$C_4$)alkoxy, halo($C_1$–$C_2$)alkyl, halo($C_1$–$C_2$)alkoxy, ($C_1$–$C_4$)alkylthio, ($C_1$–$C_4$)alkylsulfinyl, ($C_1$–$C_4$)alkylsulfonyl, carboxy, formyl, ($C_1$–$C_4$)alkylcarbonyl, ($C_1$–$C_4$)alkoxycarbonyl, ($C_1$–$C_4$)alkanoyloxy, amino, ($C_1$–$C_4$)alkylamino, di($C_1$-$C_4$)alkylamino having independently the stated number of carbon atoms in each alkyl group; or when two adjacent positions on a phenyl ring are substituted with alkoxy groups, these groups may be joined to form a 5 or 6 membered dioxolano (methylenedioxy) or dioxano (1,2-ethylenedioxy)heterocyclic ring;

$R^a$ is H, ($C_1$-$C_4$)alkyl, ($C_2$-$C_4$)alkenyl, ($C_1$-$C_4$)alkoxy, halo, cyano, nitro, halo($C_1$-$C_4$)alkyl, halo($C_1$-$C_4$)alkoxy, ($C_1$-$C_4$)alkoxy($C_1$-$C_4$)alkyl, ($C_1$-$C_4$)alkoxycarbonyl, ($C_1$-$C_4$)alkylaminocarbonyl, di($C_1$-$C_4$)alkylaminocarbonyl wherein the alkyl groups may be the same or different, cyclopropyl or cyclopropyl substituted with 1–4 of the same or different halo or ($C_1$-$C_4$)alkyl, cyclopropyl($C_1$-$C_2$)alkyl or cyclopropyl($C_1$-$C_2$)alkyl substituted on the cyclopropyl ring with 1–4 of the same or different halo or ($C_1$-$C_4$)alkyl;

Z forms a 5-membered ring together with the carbon atoms to which it is attached and is selected from the group consisting of $CR^bR^c$—$S(O)_n$—$NR^d$, $CR^bR^c$—$CR^bR^c$—O, $CR^bR^c$—$CR^bR^c$—$S(O)_n$, $CR^bR^c$—$CR^bR^c$—$NR^d$, $CR^bR^c$—$NR^d$—O, $CR^bR^c$—$NR^d$—$S(O)_n$, $CR^b$=$CR^c$—O, $CR^b$=$CR^c$—$S(O)_n$, $CR^b$=$CR^c$—$NR^d$, $CR^b$=N—$NR^d$, $CR^b$=N—O, $CR^b$=N—$CR^bR^c$, $CR^b$=N—$S(O)_n$, $CR^bR^c$—$NR^d$—$CR^bR^c$, $CR^bR^c$—O—$NR^d$, $CR^bR^c$—$S(O)_n$—$NR^d$, S—$CR^bR^c$—O, S—$CR^bR^c$—S, S—$CR^bR^c$—$NR^d$, $NR^d$—$CR^bR^c$—O, O—$CR^bR^c$—S, O—$CR^bR^c$—$NR^d$, $CR^bR^c$—O—$CR^bR^c$, $NR^d$—$CR^bR^c$—S, $NR^d$—$CR^bR^c$—$NR^e$, N=$CR^b$—O, N=$CR^b$—S, N=$CR^b$—$NR^d$, $CR^bR^c$—N=N, $NR^d$—$NR^e$—$S(O)_n$, $CR^bR^c$—$S(O)_n$—$CR^bR^c$, $CR^b$=$CR^c$—$CR^bR^c$, $CR^bR^c$—$CR^bR^c$—$CR^bR^c$, N=$CR^d$—CR $^fR^g$, N=N—O, $CR^bR^c$—S—S, $CR^bR^c$—$NR^d$—$NR^e$, $S(O)_m$—O—$CR^bR^c$, $NR^d$—$S(O)_m$—S, $NR^d$—$S(O)_m$—O, $NR^d$—N=N, $CR^bR^c$—$S(O)_m$—O and $NR^d$—$S(O)_m$—$NR^e$ wherein $R^b$ and $R^c$ are each independently H, ($C_1$-$C_4$)alkyl, halo or together with the carbon to which they are attached form carbonyl (C=O) or methylene (=$CH_2$), $R^d$ and $R^e$ are each independently H or ($C_1$-$C_4$)alkyl, $R^f$ and $R^g$ are each independently ($C_1$-$C_4$)alkyl, m is 1 or 2 and n is 0, 1 or 2; and the agronomically acceptable salts thereof.

DETAILED DESCRIPTION OF INVENTION

Alkyl is a straight chain ($C_1$-$C_4$)alkyl such as methyl, ethyl, n-propyl or n-butyl or a branched ($C_3$-$C_{10}$)alkyl such as isopropyl, isobutyl, sec-butyl, tert-butyl, isopentyl, methylneopentyl (1,2,2-trimethylpropyl), 1,1-dimethylpentyl, 1,1,3,3-tetramethylbutyl and the like.

Halo is fluoro, chloro, bromo and iodo.

Cycloalkyl is a ($C_3$-$C_6$)cycloalkyl such as cyclopropyl, cyclobutyl, cyclopentyl and cyclohexyl, all of which may be substituted with 1–4 of the same or different halo or ($C_1$-$C_4$)alkyl.

Alkoxy is straight chain or branched ($C_1$-$C_4$)alkoxy such as methoxy, ethoxy, n-propoxy, isopropoxy, n-butoxy, isobutoxy, sec-butoxy and tert-butoxy.

Haloalkyl is halo($C_1$-$C_2$)alkyl such as 1- or 2-chloroethyl, trifluoromethyl and the like.

Haloalkoxy is halo($C_1$-$C_2$)alkoxy such as 1- or 2-chloroethoxy, difluoromethoxy and the like.

Alkylthio is ($C_1$-$C_4$)alkylthio such as methylthio, n-propylthio and the like.

Alkylsulfinyl is ($C_1$-$C_4$)alkylsulfinyl such as methylsulfinyl.

Alkylsulfonyl is ($C_1$-$C_4$)alkylsulfonyl such as ethylsulfonyl.

Alkylcarbonyl is ($C_1$-$C_4$)alkylcarbonyl such as methylcarbonyl(acetyl).

Alkoxycarbonyl is ($C_1$-$C_4$)alkoxycarbonyl such methoxycarbonyl.

Alkanoyloxy is ($C_1$-$C_4$)alkanoyloxy such as methylcarbonyloxy(acetoxy).

Alkylamino is ($C_1$-$C_4$)alkylamino such as methylamino, tert-butylamino and the like.

Dialkylamino is di($C_1$-$C_4$)alkylamino such as dimethylamino, N-methyl-N-ethylamino and the like.

Alkylcarbamoyl is ($C_1$-$C_4$)alkylcarbamoyl such as methylcarbamoyl, tert-butylcarbamoyl and the like.

Dialkylcarbamoyl is di($C_1$-$C_4$)alkylamino such as dimethylcarbamoyl, N-methyl-N-ethylcarbamoyl and the like.

Cyanoalkyl is cyano($C_1$-$C_4$)alkyl such as 2-cyanoethyl, cyanomethyl and the like.

Alkoxyalkyl is ($C_1$-$C_4$)alkoxy($C_1$-$C_4$)alkyl such as methoxymethyl, 2-methoxyethyl and the like.

Alkenyl is ($C_2$-$C_6$)alkenyl such as vinyl, allyl, 2-butenyl and the like.

Alkadienyl is ($C_4$-$C_6$)alkadienyl such as 2,4-butadienyl and the like.

Alkynyl is ($C_2$-$C_6$)alkynyl such as propargyl and the like.

Alkyldithionate is ($C_1$-$C_4$)alkyldithionate such as methyldithionate and the like.

Alkylcarbonylthio is ($C_1$-$C_4$)alkylcarbonylthio such as methylcarbonylthio(acetylthio) and the like.

Trialkylsilyl is tri($C_1$-$C_4$)alkylsilyl such as trimethylsilyl, dimethyl-n-propylsilyl and the like.

Because of their very good insecticidal activity, preferred compounds of this invention are represented by formula (I) wherein $R^1$ is cyano or H;

$R^2$ is a branched ($C_3$-$C_{10}$)alkyl;

B is phenyl, naphthyl, or phenyl or naphthyl substituted with one to three of the same or different substituents selected from the group consisting of halo, cyano, nitro, thiocyanato, ($C_1$-$C_4$)alkyl, ($C_1$-$C_4$)alkoxy, halo($C_1$-$C_2$)alkyl, halo($C_1$-$C_2$)alkoxy, ($C_1$-$C_4$)alkylthio, ($C_1$-$C_4$)alkylsulfinyl, ($C_1$-$C_4$)alkylsulfonyl, carboxy, formyl, ($C_1$-$C_4$)alkylcarbonyl, ($C_1$-$C_4$)alkoxycarbonyl, ($C_1$-$C_4$)alkanoyloxy, di($C_1$-$C_4$)alkylamino having independently the stated number of carbon atoms in each alkyl group, carbamoyl, ($C_1$-$C_4$)alkylcarbamoyl, di($C_1$-$C_4$)alkylcarbamoyl having independently the stated number of carbon atoms in each alkyl group, cyano($C_1$-$C_4$)alkyl, ($C_1$-$C_4$)alkoxy($C_1$-$C_4$)alkyl, ($C_2$-$C_6$)alkenyl, ($C_4$-$C_6$)alkadienyl, ($C_2$-$C_6$)alkynyl, ($C_1$-$C_4$)alkyldithionate, ($C_1$-$C_4$)alkylcarbonylthio, tri($C_1$-$C_4$)alkylsilyl having independently the stated number of carbon atoms in each alkyl group, phenyl, phenoxy, benzoyl, phenyl($C_1$-$C_2$)alkyl or phenyl($C_1$-$C_2$)alkyl substituted on the phenyl ring with one to two of the same or different substituents selected from the group consisting of halo, cyano, nitro, hydroxy, ($C_1$-$C_4$)alkyl, ($C_1$-$C_4$)alkoxy, halo($C_1$-$C_2$)alkyl, halo($C_1$-$C_2$)alkoxy, ($C_1$-$C_4$)alkylthio, ($C_1$-$C_4$)alkylsulfinyl, ($C_1$-$C_4$)alkylsulfonyl, carboxy, formyl, ($C_1$-$C_4$)alkylcarbonyl, ($C_1$-$C_4$)alkoxycarbonyl, ($C_1$–$C_4$)alkanoyloxy, di($C_1$–$C_4$)alkylamino having independently the stated number of carbon atoms in each alkyl group; or when two adjacent positions on a phenyl ring are substituted with alkoxy groups, these groups may be joined to form a 5 or 6 membered dioxolano or dioxano heterocyclic ring;

$R^a$ is H, ($C_1$–$C_4$)alkyl, ($C_2$–$C_4$)alkenyl, ($C_1$–$C_4$)alkoxy, halo, halo($C_1$–$C_4$)alkyl, halo($C_1$–$C_4$)alkoxy, ($C_1$–$C_2$)alkoxy($C_1$–$C_2$)alkyl, cyclopropyl or cyclopropyl substituted with 1–4 of the same or different halo or ($C_1$–$C_4$)alkyl, cyclopropyl($C_1$–$C_2$)alkyl or cyclopropyl($C_1$–$C_2$)alkyl substituted on the cyclopropyl ring with 1–4 of the same or different halo or ($C_1$–$C_4$)alkyl;

Z forms a 5-membered ring together with the carbon atoms to which it is attached and is selected from the group consisting of $CR^bR^c$—$S(O)_n$—$NR^d$, $CR^bR^c$—$CR^bR^c$—O, $CR^bR^c$—$CR^bR^c$—$S(O)_n$, $CR^bR^c$—$CR^bR^c$—$NR^d$, $CR^bR^c$—$NR^d$—O, $CR^bR^c$—$NR^d$—$S(O)_n$, $CR^b$=$CR^c$—O, $CR^b$=$CR^c$—$S(O)_n$, $CR^b$=$CR^c$—$NR^d$, $CR^b$=N—$NR^d$, $CR^b$=N—O, $CR^b$=N—$CR^bR^c$, $CR^b$=N—$S(O)_n$, $CR^bR^c$—$NR^d$—$CR^bR^c$, $CR^bR^c$—O—$NR^d$, $CR^bR^c$—$S(O)_n$—NR$^d$, S—$CR^bR^c$—O, S—$CR^bR^c$—S, S—$CR^bR^c$—$NR^d$, $NR^d$—$CR^bR^c$—O, O—$CR^bR^c$—S, O—$CR^bR^c$—$NR^d$, $CR^bR^c$—O—$CR^bR^c$, $NR^d$—$CR^bR^c$—S, $NR^d$—$CR^bR^c$—$NR^e$, N=$CR^b$—O, N=$CR^b$—S, N=$CR^b$—$NR^d$, $CR^bR^c$—N=N, $NR^d$—$NR^e$—$S(O)_n$, $CR^bR^c$—$S(O)_n$— $CR^bR^c$, $CR^b$=$CR^cCR^bR^c$, $CR^bR^c$—$CR^b$=$CR^bR^c$, N=$CR^d$—$CR^fR^g$N=N—O, $CR^bR^c$—S—S, $CR^bR^c$—$NR^d$—$NR^e$, $S(O)_m$—O—$CR^bR^c$, $NR^d$—$S(O)_m$—S, $NR^d$—$S(O)_m$—O, $NR^d$—N=N, $CR^bR^c$—$S(O)_m$—O and $NR^d$—$S(O)_m$—$NR^e$ wherein $R^b$ and $R^c$ are each independently H, ($C_1$–$C_4$)alkyl, halo or together with the carbon to which they are attached form carbonyl or methylene, $R^d$ and $R^e$ are each independently H or ($C_1$–$C_4$)alkyl, $R^f$ and $R^g$ are each independently ($C_1$–$C_4$)alkyl, m is 1 or 2 and n is 0, 1 or 2.

Because of their excellent insecticidal activity, more preferred compounds of this invention are represented by formula (II)

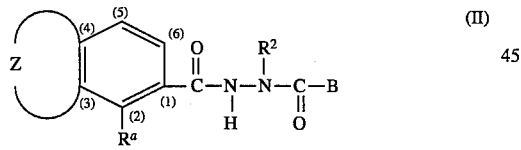

(II)

wherein $R^2$ is a branched ($C_3$—$C_8$)alkyl;

B is phenyl or phenyl substituted with one to three of the same or different substituents selected from the group consisting of halo, ($C_1$–$C_2$)alkyl, ($C_1$–$C_2$)alkoxy, halo($C_1$–$C_2$)alkyl, halo($C_1$–$C_2$)alkoxy, ($C_1$–$C_2$)alkoxy($C_1$–$C_2$)alkyl or when two adjacent positions on a phenyl ring are substituted with alkoxy groups, these groups may be joined to form a 5 or 6 membered dioxolano or dioxano heterocyclic ring;

$R^a$ is H, ($C_1$–$C_2$)alkyl, ($C_2$–$C_4$)alkenyl, ($C_1$–$C_2$)alkoxy, chloro, fluoro, chloro or polychloro($C_1$–$C_2$)alkyl, fluoro or polyfluoro($C_1$–$C_2$)alkyl, chloro or polychloro($C_1$–$C_2$)alkoxy, fluoro or polyfluoro($C_1$–$C_2$)alkoxy, ($C_1$–$C_2$)alkoxy($C_1$–$C_2$)alkyl, cyclopropyl or cyclopropyl substituted with 1–4 of the same or different chloro, fluoro or ($C_1$–$C_2$)alkyl, cyclopropyl($C_1$–$C_2$)alkyl or cyclopropyl($C_1$–$C_2$)alkyl substituted on the cyclopropyl ring with 1–4 of the same or different chloro, fluoro or ($C_1$–$C_2$)alkyl;

Z forms a 5-membered ring together with the carbon atom (3) and (4) of the substituted phenyl ring to which it is attached and is selected from the group consisting of NH—S—$CR^bR^c$, O—$CR^bR^c$—$CR^bR^c$, S—$CR^bR^c$—$CR^bR^c$, NH—$CR^bR^c$—$CR^bR^c$, O—NH—$CR^bR^c$, S—NH—$CR^bR^c$, O—$CR^b$=$CR^c$, S—$CR^b$=$CR^c$, NH—$CR^b$=$CR^c$, NH—N=$CR^b$, O—N=$CR^b$, $CR^bR^c$—N=$CR^b$, S—N=$CR^b$, $CR^bR^c$—NH—$CR^bR^c$, NH—O—$CR^bR^c$, NH—S—$CR^bR^c$, O—$CR^bR^c$—S, S—$CR^bR^c$—S, NH—$CR^bR^c$—S, O—$CR^bR^c$—NH, S—$CR^bR^c$—O, NH—$CR^bR^c$—O, $CR^bR^c$—O—$CR^bR^c$, S—$CR^bR^c$—NH, NH—$CR^bR^c$—NH, O—$CR^b$=N, S—$CR^b$=N, NH—$CR^b$=N, N=N—$CR^bR^c$, S—NH—NH, $CR^b$=$CR^c$—$CR^bR^c$, $CR^bR^c$—$CR^bR^c$—$CR^bR^c$, $CR^b R^c$—$CR^b$=$CR^c$, N=$CR^b$—$CR^fR^g$, N=N—O, N=N—NH and $CR^bR^c$—S—$CR^bR^c$ wherein $R^b$ and $R^c$ are each independently H, ($C_1$–$C_2$)alkyl, fluoro, chloro or together with the carbon to which they are attached form carbonyl or methylene, $R^f$ and $R^g$ are each independently ($C_1$–$C_2$)alkyl, and wherein the first atom of the Z-link is attached to carbon atom (3) of the phenyl ring and the last atom of the Z-link is attached to carbon atom (4) of the phenyl ring.

Because of their superior insecticidal activity, even more preferred compounds of this invention are represented by formula (II) wherein $R^2$ is tert-butyl, 1,1-dimethylpentyl or 1,1,3,3-tetramethylbutyl;

B is phenyl, 3,5-dimethylphenyl, 3-methylphenyl, 3-chlorophenyl, 3-fluorophenyl, 3,5-dichlorophenyl, 3,5-difluorophenyl, 3-chloro-5-methylphenyl or 3-fluoro-5-methylphenyl;

$R^a$ is H, ($C_1$–$C_2$)alkyl, vinyl, ($C_1$–$C_2$)alkoxy, chloro, fluoro, polychloro($C_1$–$C_2$)alkyl, polyfluoro($C_1$–$C_2$)alkyl, polyfluoro($C_1$–$C_2$)alkoxy, methoxymethyl, cyclopropyl or cyclopropyl substituted with 1–4 of the same or different fluoro or ($C_1$–$C_2$)alkyl, cyclopropyl($C_1$–$C_2$)alkyl or cyclopropyl($C_1$–$C_2$)alkyl substituted on the cyclopropyl ring with 1–4 of the same or different fluoro or ($C_1$–$C_2$)alkyl;

Z forms a 5-membered ring together with the carbon atom (3) and (4) of the substituted phenyl ring to which it is attached and is selected from the group consisting of O—$CR^bR^c$—$CR^bR^c$, S—$CR^bR^c$—$CR^bR^c$, NH—$CR^bR^c$—$CR^bR^c$, O—$CR^b$=$CR^c$, S—$CR^b$=$CR^c$, $CR^b$=$CR^c$—$CR^bR^c$, $CR^bR^c$—$CR^bR^c$—$CR^bR^c$, $CR^bR^c$—$CR^b$=$CR^c$, N=$CR^b$—$CR^fR^g$ and NH—$CR^b$=$CR^c$, wherein $R^b$ and $R^c$ are each independently H, ($C_1$–$C_2$)alkyl, fluoro, chloro or together with the carbon to which they are attached form carbonyl or methylene, $R^f$ and $R^g$ are each independently ($C_1$–$C_2$)alkyl, and wherein the first atom of the Z-link is attached to carbon atom (3) of the phenyl ring and the last atom of the Z-link is attached to carbon atom (4) of the phenyl ring.

Because of their outstanding insecticidal activity, yet even more preferred compounds of this invention are represented by formula (II) wherein $R^2$ is tert-butyl;

B is 3,5-dimethylphenyl;

$R^a$ is H, methyl, ethyl or vinyl;

Z forms a 5-membered ring together with the carbon atom (3) and (4) of the substituted phenyl ring to which it is attached and is selected from the group consisting of O—$CR^bR^c$—$CR^bR^c$, S—$CR^bR^c$—$CR^bR^c$, O—$CR^b$=$CR^c$ and S—$CR^b$=$CR^c$ wherein $R^b$ and $R^c$ are each independently H, methyl, ethyl, fluoro, or together with the carbon to which they are attached form carbonyl and wherein the first atom of the Z-link is attached to carbon atom (3) of the phenyl ring and the last atom of the Z-link is attached to carbon atom (4) of the phenyl ring.

The compounds of the present invention exhibit unexpectedly excellent results in their use as insecticides. One skilled in the art will be able to determine the activity of a given compound against a given insect and the dosage required to obtain unexpectedly good insecticidal effects. The exact dosage for a given situation can be routinely determined and the compositions and formulations for such uses, and the desired additional components (such as agronomically acceptable carriers, diluents, extenders and other common additives used in insecticidal compositions) can be determined in the known manners.

Accordingly, another embodiment is an insecticidal composition for controlling insects which comprises an agronomically acceptable carrier and an insecticidally effective amount of one or more compounds having the formula

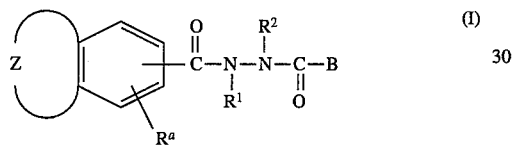

(I)

wherein $R^1$ is cyano or a hydrogen atom (H);

$R^2$ is a branched ($C_3$-$C_{10}$)alkyl or a ($C_1$-$C_4$) straight chain alkyl substituted with one or two of the same or different ($C_3$-$C_6$)cycloalkyl;

B is phenyl, naphthyl, or phenyl or naphthyl substituted with one to three of the same or different substituents selected from the group consisting of halo, cyano, nitro, hydroxy, mercapto, thiocyanato, ($C_1$-$C_4$)alkyl, ($C_1$-$C_4$)alkoxy, halo($C_1$-$C_2$)alkyl, halo($C_1$-$C_2$)alkoxy, ($C_1$-$C_4$)alkylthio, ($C_1$-$C_4$)alkylsulfinyl, ($C_1$-$C_4$)alkylsulfonyl, carboxy, formyl, ($C_1$-$C_4$)alkylcarbonyl, ($C_1$-$C_4$)alkoxycarbonyl, ($C_1$-$C_4$)alkanoyloxy, amino, ($C_1$-$C_4$)alkylamino, di($C_1$-$C_4$)alkylamino having independently the stated number of carbon atoms in each alkyl group, carbamoyl, ($C_1$-$C_4$)alkylcarbamoyl, di($C_1$-$C_4$)alkylcarbamoyl having independently the stated number of carbon atoms in each alkyl group, cyano($C_1$-$C_4$)alkyl, ($C_1$-$C_4$)alkoxy($C_1$-$C_4$)alkyl, ($C_2$-$C_6$)alkenyl, ($C_4$-$C_6$)alkadienyl, ($C_2$-$C_6$)alkynyl, ($C_1$-$C_4$)alkyldithionate, ($C_1$-$C_4$)alkylcarbonylthio, tri($C_1$-$C_4$)alkylsilyl having independently the stated number of carbon atoms in each alkyl group, phenyl, phenyl substituted with one to two of the same or different substituents selected from the group consisting of halo, cyano, nitro, hydroxy, ($C_1$-$C_4$)alkyl, ($C_1$-$C_4$)alkoxy, halo($C_1$-$C_2$)alkyl, halo($C_1$-$C_2$)alkoxy, ($C_1$-$C_4$)alkylthio, ($C_1$-$C_4$)alkylsulfinyl, ($C_1$-$C_4$)alkylsulfonyl, carboxy, formyl, ($C_1$-$C_4$)alkylcarbonyl, ($C_1$-$C_4$)alkoxycarbonyl, ($C_1$-$C_4$)alkanoyloxy, amino, ($C_1$-$C_4$)alkylamino, di($C_1$-$C_4$)alkylamino having independently the stated number of carbon atoms in each alkyl group, phenoxy, phenoxy substituted with one to two of the same or different substituents selected from the group consisting of halo, cyano, nitro, hydroxy, ($C_1$-$C_4$)alkyl, ($C_1$-$C_4$)alkoxy, halo($C_1$-$C_2$)alkyl, halo($C_1$-$C_2$)alkoxy, ($C_1$-$C_4$)alkylthio, ($C_1$-$C_4$)alkylsulfinyl, ($C_1$-$C_4$)alkylsulfonyl, carboxy, formyl, ($C_1$-$C_4$)alkylcarbonyl, ($C_1$-$C_4$)alkoxycarbonyl, ($C_1$-$C_4$)alkanoyloxy, amino, ($C_1$-$C_4$)alkylamino, di($C_1$-$C_4$)alkylamino having independently the stated number of carbon atoms in each alkyl group, benzoyl, benzoyl substituted with one to two of the same or different substituents selected from the group consisting of halo, cyano, nitro, hydroxy, ($C_1$-$C_4$)alkyl, ($C_1$-$C_4$)alkoxy, halo($C_1$-$C_2$)alkyl, halo($C_1$-$C_2$)alkoxy, ($C_1$-$C_4$)alkylthio, ($C_1$-$C_4$)alkylsulfinyl, ($C_1$-$C_4$)alkylsulfonyl, carboxy, formyl, ($C_1$-$C_4$)alkylcarbonyl, ($C_1$-$C_4$)alkoxycarbonyl, ($C_1$-$C_4$)alkanoyloxy, amino, ($C_1$-$C_4$)alkylamino, di($C_1$-$C_4$)alkylamino having independently the stated number of carbon atoms in each alkyl group, phenoxycarbonyl, phenoxycarbonyl substituted with one to two of the same or different substituents selected from the group consisting of halo, cyano, nitro, hydroxy, ($C_1$-$C_4$)alkyl, ($C_1$-$C_4$)alkoxy, halo($C_1$-$C_2$)alkyl, halo($C_1$-$C_2$)alkoxy, ($C_1$-$C_4$)alkylthio, ($C_1$-$C_4$)alkylsulfinyl, ($C_1$-$C_4$)alkylsulfonyl, carboxy, formyl, ($C_1$-$C_4$)alkylcarbonyl, ($C_1$-$C_4$)alkoxycarbonyl, ($C_1$-$C_4$)alkanoyloxy, amino, ($C_1$-$C_4$)alkylamino, di($C_1$-$C_4$)alkylamino having independently the stated number of carbon atoms in each alkyl group, phenylthio, phenylthio substituted with one to two of the same or different substituents selected from the group consisting of halo, cyano, nitro, hydroxy, ($C_1$-$C_4$)alkyl, ($C_1$-$C_4$)alkoxy, halo($C_1$-$C_2$)alkyl, halo($C_1$-$C_2$)alkoxy, ($C_1$-$C_4$)alkylthio, ($C_1$-$C_4$)alkylsulfinyl, ($C_1$-$C_4$)alkylsulfonyl, carboxy, formyl, ($C_1$-$C_4$)alkylcarbonyl, ($C_1$-$C_4$)alkoxycarbonyl, ($C_1$-$C_4$)alkanoyloxy, amino, ($C_1$-$C_4$)alkylamino, di($C_1$-$C_4$)alkylamino having independently the stated number of carbon atoms in each alkyl group, phenyl($C_1$-$C_4$)alkyl, phenyl($C_1$-$C_4$)alkyl substituted on the phenyl ring with one to two of the same or different substituents selected from the group consisting of halo, cyano, nitro, hydroxy, ($C_1$-$C_4$)alkyl, ($C_1$-$C_4$)alkoxy, halo($C_1$-$C_2$)alkyl, halo($C_1$-$C_2$)alkoxy, ($C_1$-$C_4$)alkylthio, ($C_1$-$C_4$)alkylsulfinyl, ($C_1$-$C_4$)alkylsulfonyl, carboxy, formyl, ($C_1$-$C_4$)alkylcarbonyl, ($C_1$-$C_4$)alkoxycarbonyl, ($C_1$-$C_4$)alkanoyloxy, amino, ($C_1$-$C_4$)alkylamino, di($C_1$-$C_4$)alkylamino having independently the stated number of carbon atoms in each alkyl group; or when two adjacent positions on a phenyl ring are substituted with alkoxy groups, these groups may be joined to form a 5 or 6 membered dioxolano (methylenedioxy) or dioxano (1,2-ethylenedioxy) heterocyclic ring;

$R^a$ is H, ($C_1$-$C_4$)alkyl, ($C_2$-$C_4$)alkenyl, ($C_1$-$C_4$)alkoxy, halo, cyano, nitro, halo($C_1$-$C_4$)alkyl, halo($C_1$-$C_4$)alkoxy, ($C_1$-$C_4$)alkoxy($C_1$-$C_4$)alkyl, ($C_1$-$C_4$)alkoxycarbonyl, ($C_1$-$C_4$)alkylaminocarbonyl, di($C_1$-$C_4$)alkylaminocarbonyl wherein the alkyl groups may be the same or different, cyclopropyl or cyclopropyl substituted with 1-4 of the same or different halo or ($C_1$-$C_4$)alkyl, cyclopropyl($C_1$-$C_2$)alkyl or cyclopropyl($C_1$-$C_2$)alkyl substituted on the cyclopropyl ring with 1-4 of the same or different halo or ($C_1$-$C_4$)alkyl;

Z forms a 5-membered ring together with the carbon atoms to which it is attached and is selected from the group consisting of $CR^bR^c$—$S(O)_n$—$NR^d$, $CR^bR^c$—$CR^bR^c$—O, $CR^bR^c$—$CR^bR^c$—$S(O)_n$, $CR^bR^c$—$CR^b R^c$—$NR^d$, $CR^bR^c$—$NR^d$—O, $CR^bR^c$—$NR^d$—$S(O)_n$, $CR^b$=$CR^c$—O, $CR^b$=$CR^c$—$S(O)_n$, $CR^b$=$CR^c$—$NR^d$, $CR^b$=N—$NR^d$, $CR^b$=N—O, $CR^b$=N—$CR^bR^c$, $CR^b$=N—$S(O)_n$, $CR^bR^c$—$NR^d$—$CR^bR^c$, $CR^bR^c$—O—$NR^d$, $CR^bR^c$—$S(O)_n$—$NR^d$, S—$CR^bR^c$—O, S—$CR^bR^c$—S, S—$CR^bR^c$—$NR^d$, $NR^d$—$CR^bR^c$—O, O—$CR^bR^c$—S, O—$CR^bR^c$—$NR^d$, $CR^bR^c$—O—$CR^bR^c$, $NR^d$—$CR^bR^c$—S, $NR^d$—$CR^bR^c$—$NR^e$, N=$CR^b$—O, N=$CR^b$—S, N=$CR^b$—$NR^d$, $CR^bR^c$—N=N, $NR^d$—$NR^e$—$S(O)_n$, $CR^bR^c$—$S(O)_n$—$CR^bR^c$, $CR^b$=$CR^c$—$CR^bR^c$, $CR^bR^c$—$CR^bR^c$—$CR^bR^c$, N=$CR^d$—$CR^fR^g$, N=N—O, $CR^bR^c$—S—S, $CR^bR^c$—$NR^d$—$NR^e$, $S(O)_m$—O—$CR^bR^c$, $NR^d$—$S(O)_m$—S, $NR^d$—$S(O)_m$—O, $NR^d$—N=N, $CR^bR^c$—$S(O)_m$—O and $NR^d$—$S(O)_m$—$NR^e$ wherein $R^b$ and $R^c$ are each independently H, $(C_1-C_4)$alkyl, halo or together with the carbon to which they are attached form carbonyl (C=O) or methylene (=$CH_2$), $R^d$ and $R^e$ are each independently H or $(C_1-C_4)$alkyl, $R^f$ and $R^g$ are each independently $(C_1-C_4)$alkyl, m is 1 or 2 and n is 0, 1 or 2; and the agronomically acceptable salts thereof.

The preferred compositions have the preferred compounds set out hereinabove.

Also embodied is a method for controlling insects comprising contacting the insect with an insecticidally effective amount of a compound having the formula

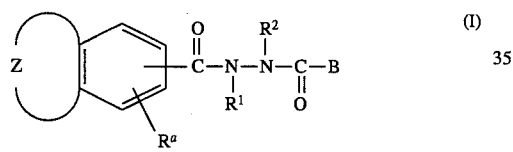

(I)

wherein $R^1$ is cyano or a hydrogen atom (H);

$R^2$ is a branched $(C_3-C_{10})$alkyl or a $(C_1-C_4)$ straight chain alkyl substituted with one or two of the same or different $(C_3-C_6)$cycloalkyl;

B is phenyl, naphthyl, or phenyl or naphthyl substituted with one to three of the same or different substituents selected from the group consisting of halo, cyano, nitro, hydroxy, mercapto, thiocyanato, $(C_1-C_4)$alkyl, $(C_1-C_4)$alkoxy, halo$(C_1-C_2)$alkyl, halo$(C_1-C_2)$alkoxy, $(C_1-C_4)$alkylthio, $(C_1-C_4)$alkylsulfinyl, $(C_1-C_4)$alkylsulfonyl, carboxy, formyl, $(C_1-C_4)$alkylcarbonyl, $(C_1-C_4)$alkoxycarbonyl, $(C_1-C_4)$alkanoyloxy, amino, $(C_1-C_4)$alkylamino, di$(C_1-C_4)$alkylamino having independently the stated number of carbon atoms in each alkyl group, carbamoyl, $(C_1-C_4)$alkylcarbamoyl, di$(C_1-C_4)$alkylcarbamoyl having independently the stated number of carbon atoms in each alkyl group, cyano$(C_1-C_4)$alkyl, $(C_1-C_4)$alkoxy$(C_1-C_4)$alkyl, $(C_2-C_6)$alkenyl, $(C_4-C_6)$alkadienyl, $(C_2-C_6)$alkynyl, $(C_1-C_4)$alkyldithionate, $(C_1-C_4)$alkylcarbonylthio, tri$(C_1-C_4)$alkylsilyl having independently the stated number of carbon atoms in each alkyl group, phenyl, phenyl substituted with one to two of the same or different substituents selected from the group consisting of halo, cyano, nitro, hydroxy, $(C_1-C_4)$alkyl, $(C_1-C_4)$alkoxy, halo$(C_1-C_2)$alkyl, halo$(C_1-C_2)$alkoxy, $(C_1-C_4)$alkylthio, $(C_1-C_4)$alkylsulfinyl, $(C_1-C_4)$alkylsulfonyl, carboxy, formyl, $(C_1-C_4)$alkylcarbonyl, $(C_1-C_4)$alkoxycarbonyl, $(C_1-C_4)$alkanoyloxy, amino, $(C_1-C_4)$alkylamino, di$(C_1-C_4)$alkylamino having independently the stated number of carbon atoms in each alkyl group, phenoxy, phenoxy substituted with one to two of the same or different substituents selected from the group consisting of halo, cyano, nitro, hydroxy, $(C_1-C_4)$alkyl, $(C_1-C_4)$alkoxy, halo$(C_1-C_2)$alkyl, halo$(C_1-C_2)$alkoxy, $(C_1-C_4)$alkylthio, $(C_1-C_4)$alkylsulfinyl, $(C_1-C_4)$alkylsulfonyl, carboxy, formyl, $(C_1-C_4)$alkylcarbonyl, $(C_1-C_4)$alkoxycarbonyl, $(C_1-C_4)$alkanoyloxy, amino, $(C_1-C_4)$alkylamino, di$(C_1-C_4)$alkylamino having independently the stated number of carbon atoms in each alkyl group, benzoyl, benzoyl substituted with one to two of the same or different substituents selected from the group consisting of halo, cyano, nitro, hydroxy, $(C_1-C_4)$alkyl, $(C_1-C_4)$alkoxy, halo$(C_1-C_2)$alkyl, halo$(C_1-C_2)$alkoxy, $(C_1-C_4)$alkylthio, $(C_1-C_4)$alkylsulfinyl, $(C_1-C_4)$alkylsulfonyl, carboxy, formyl, $(C_1-C_4)$alkylcarbonyl, $(C_1-C_4)$alkoxycarbonyl, $(C_1-C_4)$alkanoyloxy, amino, $(C_1-C_4)$alkylamino, di$(C_1-C_4)$alkylamino having independently the stated number of carbon atoms in each alkyl group, phenoxycarbonyl, phenoxycarbonyl substituted with one to two of the same or different substituents selected from the group consisting of halo, cyano, nitro, hydroxy, $(C_1-C_4)$alkyl, $(C_1-C_4)$alkoxy, halo $(C_1-C_2)$alkyl, halo$(C_1-C_2)$alkoxy, $(C_1-C_4)$alkylthio, $(C_1-C_4)$alkylsulfinyl, $(C_1-C_4)$alkylsulfonyl, carboxy, formyl, $(C_1-C_4)$alkylcarbonyl, $(C_1-C_4)$alkoxycarbonyl, $(C_1-C_4)$alkanoyloxy, amino, $(C_1-C_4)$alkylamino, di$(C_1-C_4)$alkylamino having independently the stated number of carbon atoms in each alkyl group, phenylthio, phenylthio substituted with one to two of the same or different substituents selected from the group consisting of halo, cyano, nitro, hydroxy, $(C_1-C_4)$alkyl, $(C_1-C_4)$alkoxy, halo$(C_1-C_2)$alkyl, halo$(C_1-C_2)$alkoxy, $(C_1-C_4)$alkylthio, $(C_1-C_4)$alkylsulfinyl, $(C_1-C_4)$alkylsulfonyl, carboxy, formyl, $(C_1-C_4)$alkylcarbonyl, $(C_1-C_4)$alkoxycarbonyl, $(C_1-C_4)$alkanoyloxy, amino, $(C_1-C_4)$alkylamino, di$(C_1-C_4)$alkylamino having independently the stated number of carbon atoms in each alkyl group, phenyl$(C_1-C_4)$alkyl, phenyl$(C_1-C_4)$alkyl substituted on the phenyl ring with one to two of the same or different substituents selected from the group consisting of halo, cyano, nitro, hydroxy, $(C_1-C_4)$alkyl, $(C_1-C_4)$alkoxy, halo$(C_1-C_2)$alkyl, halo$(C_1-C_2)$alkoxy, $(C_1-C_4)$alkylthio, $(C_1-C_4)$alkylsulfinyl, $(C_1-C_4)$alkylsulfonyl, carboxy, formyl, $(C_1-C_4)$alkylcarbonyl, $(C_1-C_4)$alkoxycarbonyl, $(C_1-C_4)$alkanoyloxy, amino, $(C_1-C_4)$alkylamino, di$(C_1-C_4)$alkylamino having independently the stated number of carbon atoms in each alkyl group; or when two adjacent positions on a phenyl ring are substituted with alkoxy groups, these groups may be joined to form a 5 or 6 membered dioxolano (methylenedioxy) or dioxano (1,2-ethylenedioxy)heterocyclic ring;

$R^a$ is H, $(C_1-C_4)$alkyl, $(C_2-C_4)$alkenyl, $(C_1-C_4)$alkoxy, halo, cyano, nitro, halo$(C_1-C_4)$alkyl, halo$(C_1-C_4)$alkoxy, $(C_1-C_4)$alkoxy$(C_1-C_4)$alkyl, $(C_1-C_4)$alkoxycarbonyl, $(C_1-C_4)$alkylaminocarbonyl, di$(C_1-C_4)$alkylaminocarbonyl wherein the alkyl groups may be the same or different, cyclopropyl or cyclopropyl substituted with 1–4 of the same or different halo or $(C_1-C_4)$alkyl, cyclopropyl$(C_1-C_2)$alkyl or cyclopropyl$(C_1-C_2)$alkyl substituted on the cyclopropyl ring with 1–4 of the same or different halo or $(C_1-C_4)$alkyl;

Z forms a 5-membered ring together with the carbon atoms to which it is attached and is selected from the group consisting of $CR^bR^c$—$S(O)_n$—$NR^d$, $CR^bR^c$—$CR^bR^c$—O, $CR^bR^c$—$CR^bR^c$—$S(O)_n$, $CR^bR^c$—$CR^b R^c$—$NR^d$, $CR^bR^c$—$NR^d$—O, $CR^bR^c$—$NR^dS(O)_n$, $CR^b$=$CR^c$—O, $CR^b$=$CR^c$—$S(O)_n$, $CR^b$=$CR^c$—$NR^d$, $CR^b$=N—$NR^d$, $CR^b$=N—O, $CR^b$=N—$CR^bR^c$, $CR^b$=N—$S(O)_n$, $CR^bR^c$—$NR^d$—$CR^bR^c$, $CR^bR^c$—O—$NR^d$, $CR^bR^c$—$S(O)_n$—$NR^d$, S—$CR^bR^c$—O, S—$CR^bR^c$—S, S—$CR^bR^c$—$NR^d$, $NR^d$—$CR^bR^c$—O, O—$CR^bR^c$—S, O—$CR^bR^c$—$NR^d$, $CR^bR^c$—O—$CR^bR^c$, $NR^d$—$CR^bR^c$—S, $NR^d$—$CR^bR^c$—$NR^e$, N=$CR^b$—O, N=$CR^b$—S, N=$CR^b$—$NR^d$, $CR^bR^c$—N=N, $NR^d$—$NR^e$—$S(O)_n$, $CR^bR^c$—$S(O)_n$—$CR^bR^c$, $CR^b$=$CR^c$—$CR^bR^c$, $CR^bR^c$—$CR^bR^c$—$CR^bR^c$, N=$CR^d$—$CR^fR^g$, N=N—O, $CR^bR^c$—S—S, $CR^bR^c$—$NR^d$—$NR^e$, $S(O)_m$—O—$CR^bR^c$, $NR^d$—$S(O)_m$—S, $NR^d$—$S(O)_m$—O, $NR^d$—N=N, $CR^bR^c$—$S(O)_m$O and $NR^d$—$S(O)_m$—$NR^e$ wherein $R^b$ and $R^c$ are each independently H, $(C_1-C_4)$alkyl, halo or together with the carbon to which they are attached form carbonyl (C=O) or methylene (=$CH_2$), $R^d$ and $R^e$ are each independently H or $(C_1-C_4)$alkyl, $R^f$ and $R^g$ are each independently $(C_1-C_4)$alkyl, m is 1 or 2 and n is 0, 1 or 2; and the agronomically acceptable salts thereof.

The preferred methods will utilize the preferred compounds hereinabove identified.

METHODS OF PREPARATION

Many of the compounds of the present invention, and the intermediates related thereto, can be prepared by methods similar to the known methods, such as those taught by U.S. Pat. No. 5,117,057, for making N,N'-disubstituted-N,N'-diacylhydrazines. In particular, Process B—Method 2 was used to prepare the compounds of Table I. Those of ordinary skill in the art will be able to utilize or modify such processes after knowledge of the disclosures herein to accommodate many of the functionalities $R^1$, $R^2$, $R^a$, B and Z in the intermediates and compounds of the present invention. The agronomically acceptable salts of the present insecticidal compounds can be synthesized by the utilization of the salting methods known in the art relating to N'-substituted-N,N'-diacylhydrazines used as insecticides.

Preparation of 6-carboxymethyl-2,2-dimethyl-dihydrobenzofuran and 6-carboxymethyl-1-methyl-benzofuran Using procedures analogous to those of D. W. Robertson, et. al., *J. Med. Chem.*, 35, 310 (1992) and V. Peesapati, and N. Lingaiah, *Org. Prep. Proc. Int.*, 24(1), 27 (1992), the hydroxy group of methyl 3-hydroxybenzoate was alkylated with 3-chloro-2-methyl-1-propene to give methyl 3-(2-methyl-2-propenyloxy)benzoate. This material then underwent a 3,3 sigmatrophic shift to give methyl 3-hydroxy-4-(2-methyl-2-propenyl)benzoate. Formic acid catalyzed ring closure resulted in 2,2-dimethyl-6-carboxymethyl-dihydrobenzofuran.

By using 2,3-dichloropropene instead of 3-chloro-2-methyl-1-propene as the alkylating agent, the same procedure provides 6-carboxymethyl-1-methyl-benzofuran.

Preparation of 6-Carboxy-benzofuran and 6-Carboxy-dihydrobenzofuran

6-Carboxy-benzofuran was prepared from methyl 4-formyl-3-hydroxy-benzoate using the procedure of F. Duro and P. Condorelli, *Ann. Chim. (Roma)*, 53(11), 1582 (1963). The corresponding dihydrobenzofuran was prepared by catalytic hydrogenation of the benzofuran in a Parr apparatus using ethyl acetate as the solvent and platinum oxide catalyst.

Preparation of 7-substituted-6-carboxy-dihydrobenzofuran

6-Carboxy-dihydrobenzofuran was first treated with thionyl chloride to give the acid chloride. The acid chloride was then treated with 2-amino-2-methylpropanol to give an intermediate amide which was cyclized to 6-(4,4-dimethyl-2-oxazolyl)dihydrobenzofuran by treatment with thionyl chloride, both steps using the procedure described in A. Meyers and W. Avila, *J. Org. Chem.*, 46, 3881 (1981). This procedure also describes methylation at the 7-position using butyl lithium and methyl iodide. Subsequent acid catalyzed hydrolysis of the oxazoline results in formation of the 7-substituted-6-dihydrobenzofuran.

Preparation of 7-substituted and 2-substituted-6-carboxy-benzofurans

6-Carboxy-benzofuran was treated with 2.2 equivalents of butyl lithium in tetrahydrofuran at −65° to −70° C. followed by addition of ethyl iodide and permitting the reaction mixture to warm to room temperature. This process resulted in a mixture of the 7- and 2-ethyl substituted 6-carboxybenzofurans. These two isomers were not separated at this time. However, after formation of the corresponding N-substituted-N,N'-diacylhydrazines, as described below, the isomers were separated as the diacylhydrazine derivatives using silica gel chromatography with methylene chloride-:ethyl acetate 9:1 elution solvent.

Preparation of N-substituted-N,N'-diacylhydrazines

The N-substituted-N,N'-diacylhydrazines corresponding to the above carboxybenzofurans were prepared in a two step process. The first step is the formation of the acid chloride. With the exception of 2,2-dimethyl-6-carboxy-dihydrobenzofuran, which required the use of oxalyl chloride, the acid chlorides can be prepared using standard methods known in the art using thionyl chloride, oxalyl chloide, phosphorous pentachloride, and the like, as the chlorinating agent.

Reaction of the acid chloride with N-tert-butyl-N-(3,5-dimethylbenzoyl)hydrazine in an inert solvent such as dichloromethane or butyl acetate and potassium carbonate resulted in formation of the corresponding N-substituted-N,N'-diacylhydrazines of formula I wherein the Z substituent forms a fused furan or dihydrofuran ring.

TABLE I

COMPOUNDS OF THIS INVENTION

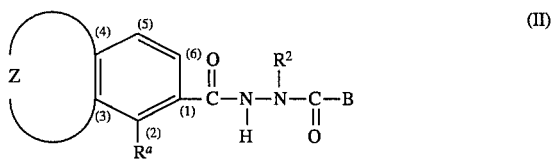

(II)

| No. | Z | $R^a$ | $R^2$ | B | Mp. °C. |
|---|---|---|---|---|---|
| 1 | O—CH=CH | H | —C(CH$_3$)$_3$ | 3,5-Dimethylphenyl | 176–178 |
| 2 | O—CH=CH | C$_2$H$_5$ | —C(CH$_3$)$_3$ | 3,5-Dimethylphenyl | 105 |
| 3 | O—C(C$_2$H$_5$)=CH | H | —C(CH$_3$)$_3$ | 3,5-Dimethylphenyl | 187–189 |
| 4 | O—CH$_2$—CH$_2$ | H | —C(CH$_3$)$_3$ | 3,5-Dimethylphenyl | 183–184 |
| 5 | O—C(CH$_3$)=CH | H | —C(CH$_3$)$_3$ | 3,5-Dimethylphenyl | 204–205 |
| 6 | O—C(CH$_3$)$_2$—CH$_2$ | H | —C(CH$_3$)$_3$ | 3,5-Dimethylphenyl | 118 |
| 7 | O—CH$_2$—CH$_2$ | CH$_3$ | —C(CH$_3$)$_3$ | 3,5-Dimethylphenyl | 125–130 |

Other compounds contemplated by this invention are listed in Table II. Compounds wherein $R^1$ is cyano are prepared from the corresponding diacylhydrazine wherein $R^1$ is hydrogen using the method described in U.S. Pat. No. 4,857,550. These compounds further exemplify, but do not limit, the scope of this invention.

TABLE II

REPRESENTATIVE COMPOUNDS OF THIS INVENTION

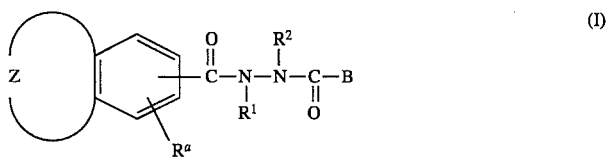

(I)

| No. | Z | $R^a$ | $R^1$ | $R^2$ | B |
|---|---|---|---|---|---|
| a | S—CH$_2$—CH$_2$ | H | H | —C(CH$_3$)$_3$ | 3,5-dimethylphenyl |
| b | S—CH$_2$—CH$_2$ | CH$_3$ | H | —C(CH$_3$)$_3$ | 3,5-dimethylphenyl |
| c | S—CH$_2$—CH$_2$ | CH$_2$CH$_3$ | H | —C(CH$_3$)$_3$ | 3,5-dimethylphenyl |
| d | S—CH$_2$—CH$_2$ | CH=CH$_2$ | H | —C(CH$_3$)$_3$ | 3,5-dimethylphenyl |
| e | O—CH$_2$—CH$_2$ | CH$_3$ | CN | —C(CH$_3$)$_3$ | 3,5-dimethylphenyl |
| f | O—CH=CH | CH$_3$ | CN | —C(CH$_3$)$_3$ | 3-chloro-5-methylphenyl |
| g | S—CH=CH | CH$_3$ | H | —C(CH$_3$)$_3$ | 3,5-dimethylphenyl |
| h | CH=CHCH$_2$ | H | H | —C(CH$_3$)$_3$ | 3,5-dimethylphenyl |
| i | NHCH=CH | CH$_2$CH$_3$ | H | —C(CH$_3$)$_3$ | 3,5-dimethylphenyl |
| j | NHCH$_2$NH | CH$_3$ | H | —C(CH$_3$)$_3$ | 3,5-dimethylphenyl |
| k | CH$_2$C(O)O | H | H | —C(CH$_3$)$_3$ | 3,5-dimethylphenyl |
| l | O—CH=N | H | H | —C(CH$_3$)$_3$ | 3,5-dimethylphenyl |
| m | S—CH$_2$—CH$_2$ | CH=CH$_2$ | H | —C(CH$_3$)$_2$C$_4$H$_9$ | 3-methylphenyl |
| n | O—CH$_2$—CH$_2$ | CH$_3$ | CN | —C(CH$_3$)$_3$ | 3-chlorophenyl |
| o | O—CH=CH | CH$_3$ | CN | —C(CH$_3$)$_3$ | 3-fluorophenyl |
| p | S—CH=CH | CH$_3$ | H | —C$_8$H$_{17}$ | 3-fluoro-5-methylphenyl |
| q | OCH$_2$CH(CH$_3$) | H | H | —C(CH$_3$)$_2$C$_4$H$_9$ | 3-methylphenyl |
| r | NHCH=CH | CH$_2$CH$_3$ | H | —C(CH$_3$)$_3$ | 3-chlorophenyl |
| s | OCH(CH$_3$)CH$_2$ | CH$_3$ | H | —C(CH$_3$)$_3$ | 3-fluorophenyl |
| t | S—CH=N | H | H | —C$_8$H$_{17}$ | phenyl |
| u | O—CH=N | CH=CH$_2$ | H | —C(CH$_3$)$_2$C$_4$H$_9$ | phenyl |
| v | O—CH$_2$—CH$_2$ | CH$_3$ | H | —C(CH$_3$)$_3$ | phenyl |
| w | CH$_2$C(=CH$_2$)O | H | H | —C(CH$_3$)$_3$ | 3,5-dimethylphenyl |
| x | O—CH=CH | CH$_3$ | CN | —C(CH$_3$)$_3$ | 3-methoxyphenyl |
| y | CF$_2$CF$_2$O | CH$_3$ | H | —C(CH$_3$)$_3$ | 3-chloro-5-methoxyphenyl |
| z | C(Cl)=CHO | CH$_2$CH$_3$ | H | —C(CH$_3$)$_3$ | 3-methylphenyl |

It should be understood that the instant specification and examples are set forth by way of illustration and not limitation, and that various modifications and changes may be made without departing from the spirit and scope of the present invention as defined by the appended claims.

I claim:

1. An insecticidal compound having the formula

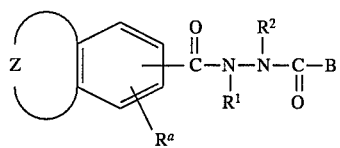

wherein
R$^1$ is cyano or a hydrogen atom (H);
R$^2$ is a branched (C$_3$–C$_{10}$)alkyl or a (C$_1$–C$_4$) straight chain alkyl substituted with one or two of the same or different (C$_3$–C$_6$)cycloalkyl;

B is phenyl, naphthyl, or phenyl or naphthyl substituted with one to three of the same or different substituents selected from the group consisting of halo, cyano, nitro, hydroxy, mercapto, thiocyanato, (C$_1$–C$_4$)alkyl, (C$_1$–C$_4$)alkoxy, halo(C$_1$–C$_2$)alkyl, halo(C$_1$–C$_2$)alkoxy, (C$_1$–C$_4$)alkylthio, (C$_1$–C$_4$)alkylsulfinyl, (C$_1$–C$_4$)alkylsulfonyl, carboxy, formyl, (C$_1$–C$_4$)alkylcarbonyl, (C$_1$–C$_4$)alkoxycarbonyl, (C$_1$–C$_4$)alkanoyloxy, amino, (C$_1$–C$_4$)alkylamino, di(C$_1$–C$_4$)alkylamino having independently the stated number of carbon atoms in each alkyl group, carbamoyl, (C$_1$–C$_4$)alkylcarbamoyl, di(C$_1$–C$_4$)alkylcarbamoyl having independently the stated number of carbon atoms in each alkyl group, cyano(C$_1$–C$_4$)alkyl, (C$_1$–C$_4$)alkoxy(C$_1$–C$_4$)alkyl, (C$_2$–C$_6$)alkenyl, (C$_4$–C$_6$)alkadienyl, (C$_2$–C$_6$)alkynyl, (C$_1$–C$_4$)alkyldithionate, (C$_1$–C$_4$)alkylcarbonylthio, tri(C$_1$–C$_4$)alkylsilyl having independently the stated number of carbon atoms in each alkyl group, phenyl, phenyl substituted with one to two of the same or different substituents selected from the group consisting of halo, cyano, nitro, hydroxy, (C$_1$–C$_4$)alkyl, (C$_1$–C$_4$)alkoxy, halo (C$_1$–C$_2$)alkyl, halo(C$_1$–C$_2$)alkoxy, (C$_1$–C$_4$)alkylthio, (C$_1$–C$_4$)alkylsulfinyl, (C$_1$–C$_4$)alkylsulfonyl, carboxy, formyl, (C$_1$–C$_4$)alkylcarbonyl, (C$_1$–C$_4$)alkoxycarbonyl, (C$_1$–C$_4$)alkanoyloxy, amino, (C$_1$–C$_4$)alkylamino and di(C$_1$–C$_4$)alkylamino having independently the stated number of carbon atoms in each alkyl group, phenoxy, phenoxy substituted with one to two of the same or different substituents selected from the group consisting of halo, cyano, nitro, hydroxy, (C$_1$–C$_4$)alkyl, (C$_1$–C$_4$)alkoxy, halo(C$_1$–C$_2$)alkyl, halo(C$_1$–C$_2$)alkoxy, (C$_1$–C$_4$)alkylthio, (C$_1$–C$_4$)alkylsulfinyl, (C$_1$–C$_4$)alkylsulfonyl, carboxy, formyl, (C$_1$–C$_4$)alkylcarbonyl, (C$_1$–C$_4$)alkoxycarbonyl, (C$_1$–C$_4$)alkanoyloxy, amino, (C$_1$–C$_4$)alkylamino and di(C$_1$–C$_4$)alkylamino having independently the stated number of carbon atoms in each alkyl group, benzoyl, benzoyl substituted with one to two of the same or different substituents selected from the group consisting of halo, cyano, nitro, hydroxy, (C$_1$–C$_4$)alkyl, (C$_1$–C$_4$)alkoxy, halo(C$_1$–C$_2$)alkyl, halo(C$_1$–C$_2$)alkoxy, (C$_1$–C$_4$)alkylthio, (C$_1$–C$_4$)alkylsulfinyl, (C$_1$–C$_4$)alkylsulfonyl, carboxy, formyl, (C$_1$–C$_4$)alkylcarbonyl, (C$_1$–C$_4$)alkoxycarbonyl, (C$_1$–C$_4$)alkanoyloxy, amino, (C$_1$–C$_4$)alkylamino and di(C$_1$–C$_4$)alkylamino having independently the stated number of carbon atoms in each alkyl group, phenoxycarbonyl, phenoxycarbonyl substituted with one to two of the same or different substituents selected from the group consisting of halo, cyano, nitro, hydroxy, (C$_1$–C$_4$)alkyl, (C$_1$–C$_4$)alkoxy, halo (C$_1$–C$_2$)alkyl, halo (C$_1$–C$_2$)alkoxy, (C$_1$–C$_4$)alkylthio, (C$_1$–C$_4$)alkylsulfinyl, (C$_1$–C$_4$)alkylsulfonyl, carboxy, formyl, (C$_1$–C$_4$)alkylcarbonyl, (C$_1$–C$_4$)alkoxycarbonyl, (C$_1$–C$_4$)alkanoyloxy, amino, (C$_1$–C$_4$)alkylamino and di(C$_1$–C$_4$)alkylamino having independently the stated number of carbon atoms in each alkyl group, phenylthio, phenylthio substituted with one to two of the same or different substituents selected from the group consisting of halo, cyano, nitro, hydroxy, (C$_1$–C$_4$)alkyl, (C$_1$–C$_4$)alkoxy, halo(C$_1$–C$_2$)alkyl, halo(C$_1$–C$_2$)alkoxy, (C$_1$–C$_4$)alkylthio, (C$_1$–C$_4$)alkylsulfinyl, (C$_1$–C$_4$)alkylsulfonyl, carboxy, formyl, (C$_1$–C$_4$)alkylcarbonyl, (C$_1$–C$_4$)alkoxycarbonyl, (C$_1$–C$_4$)alkanoyloxy, amino, (C$_1$–C$_4$)alkylamino and di(C$_1$–C$_4$)alkylamino having independently the stated number of carbon atoms in each alkyl group, phenyl(C$_1$–C$_4$)alkyl, phenyl(C$_1$–C$_4$)alkyl substituted on the phenyl ring with one to two of the same or different substituents selected from the group consisting of halo, cyano, nitro, hydroxy, (C$_1$–C$_4$)alkyl, (C$_1$–C$_4$)alkoxy, halo(C$_1$–C$_2$)alkyl, halo(C$_1$–C$_2$)alkoxy, (C$_1$–C$_4$)alkylthio, (C$_1$–C$_4$)alkylsulfinyl, (C$_1$–C$_4$)alkylsulfonyl, carboxy, formyl, (C$_1$–C$_4$)alkylcarbonyl, (C$_1$–C$_4$)alkoxycarbonyl, (C$_1$–C$_4$)alkanoyloxy, amino, (C$_1$–C$_4$)alkylamino and di(C$_1$–C$_4$)alkylamino having independently the stated number of carbon atoms in each alkyl group; or when two adjacent positions on a phenyl ring are substituted with alkoxy groups, these groups may be joined to form a 5 or 6 membered dioxolano (methylenedioxy) or dioxano (1,2-ethylenedioxy) heterocyclic ring;

R$^a$ is H, (C$_1$–C$_4$)alkyl, (C$_2$–C$_4$)alkenyl, (C$_1$–C$_4$)alkoxy, halo, cyano, nitro, halo(C$_1$–C$_4$)alkyl, halo(C$_1$–C$_4$)alkoxy, (C$_1$–C$_4$)alkoxy(C$_1$–C$_4$)alkyl, (C$_1$–C$_4$)alkoxycarbonyl, (C$_1$–C$_4$)alkylaminocarbonyl, di(C$_1$–C$_4$)alkylaminocarbonyl wherein the alkyl groups may be the same or different, cyclopropyl or cyclopropyl substituted with 1–4 of the same or different halo or (C$_1$–C$_4$)alkyl, cyclopropyl(C$_1$–C$_2$)alkyl or cyclopropyl(C$_1$–C$_2$)alkyl substituted on the cyclopropyl ring with 1–4 of the same or different halo or (C$_1$–C$_4$)alkyl;

Z forms a 5-membered ring together with the carbon atoms to which it is attached and is selected from the group consisting of CR$^b$R$^c$—S(O)$_n$—NR$^d$, CR$^b$R$^c$—CR$^b$R$^c$—S(O)$_n$ wherein n is 1 or 2, CR$^b$R$^c$—CR$^b$R$^c$—NR$^d$, CR$^b$R$^c$—NR$^d$—O, CR$^b$R$^c$—NR$^d$—S(O)$_n$, CR$^b$=CR$^c$—S(O)$_n$ wherein n is 1 or 2, CR$^b$=CR$^c$—NR$^d$, CR$^b$=N—NR$^d$, CR$^b$=N—O, CR$^b$=N—CR$^b$R$^c$, CR$^b$=N—S(O)$_n$, CR$^b$R$^c$—NR$^d$—CR$^b$R$^c$, CR$^b$R$^c$—O—NR$^d$, CR$^b$R$^c$—S(O)$_n$—NR$^d$, S—CR$^b$R$^c$—O, S—CR$^b$R$^c$—S, S—CR$^b$R$^c$—NR$^d$, NR$^d$—CR$^b$R$^c$—O, O—CR$^b$R$^c$—S, O—CR$^b$R$^c$—NR$^d$, NR$^d$—CR$^b$R$^c$—S, NR$^d$—CR$^b$R$^c$—NR$^e$, N=CR$^b$—O, N=CR$^b$—NR$^d$, CR$^b$R$^c$—N=N, NR$^d$—NR$^e$—S(O)$_n$, CR$^b$R$^c$—S(O)$_n$—CR$^b$R$^c$ wherein n is 1 or 2, CR$^b$=CR$^c$—CR$^b$R$^c$, N=CR$^d$—CR$^f$R$^g$, N=N—O, CR$^b$R$^c$—S—S, CR$^b$R$^c$—NR$^d$—

NR$^e$, S(O)$_m$—O—CR$^b$R$^c$, NR$^d$—S(O)$_m$—S, NR$^d$—S(O)$_m$—O, NR$^d$—N=N, CR$^b$R$^c$—S(O)$_m$—O and NR$^d$—S(O)$_m$—NR$^e$ wherein R$^b$ and R$^c$ are each independently H, (C$_1$–C$_4$)alkyl, halo or together with the carbon to which they are attached form carbonyl (C=O) or methylene (=CH$_2$), R$^d$ and R$^e$ are each independently H or (C$_1$–C$_4$)alkyl, R$^f$ and R$^g$ are each independently (C$_1$–C$_4$)alkyl, m is 1 or 2 and n is 0, 1 or 2; and the agronomically acceptable salts thereof.

2. The compound of claim 1, wherein

R$^1$ is cyano or H;

R$^2$ is a branched (C$_3$–C$_{10}$)alkyl;

B is phenyl, naphthyl, or phenyl or naphthyl substituted with one to three of the same or different substituents selected from the group consisting of halo, cyano, nitro, thiocyanato, (C$_1$–C$_4$)alkyl, (C$_1$–C$_4$)alkoxy, halo(C$_1$–C$_2$)alkyl, halo(C$_1$–C$_2$)alkoxy, (C$_1$–C$_4$)alkylthio, (C$_1$–C$_4$)alkylsulfinyl, (C$_1$–C$_4$)alkylsulfonyl, carboxy, formyl, (C$_1$–C$_4$)alkylcarbonyl, (C$_1$–C$_4$)alkoxycarbonyl, (C$_1$–C$_4$)alkanoyloxy, di(C$_1$–C$_4$)alkylamino having independently the stated number of carbon atoms in each alkyl group, carbamoyl, (C$_1$–C$_4$)alkylcarbamoyl, di(C$_1$–C$_4$)alkylcarbamoyl having independently the stated number of carbon atoms in each alkyl group, cyano(C$_1$–C$_4$)alkyl, (C$_1$–C$_4$)alkoxy(C$_1$–C$_4$)alkyl, (C$_2$–C$_6$)alkenyl, (C$_4$–C$_6$)alkadienyl, (C$_2$–C$_6$)alkynyl, (C$_1$–C$_4$)alkyldithionate, (C$_1$–C$_4$)alkylcarbonylthio, tri(C$_1$–C$_4$)alkylsilyl having independently the stated number of carbon atoms in each alkyl group, phenyl, phenoxy, benzoyl, phenyl(C$_1$–C$_2$)alkyl or phenyl(C$_1$–C$_2$)alkyl substituted on the phenyl ring with one to two of the same or different substituents selected from the group consisting of halo, cyano, nitro, hydroxy, (C$_1$–C$_4$)alkyl, (C$_1$–C$_4$)alkoxy, halo(C$_1$–C$_2$)alkyl, halo(C$_1$–C$_2$)alkoxy, (C$_1$–C$_4$)alkylthio, (C$_1$–C$_4$)alkylsulfinyl, (C$_1$–C$_4$)alkylsulfonyl, carboxy, formyl, (C$_1$–C$_4$)alkylcarbonyl, (C$_1$–C$_4$)alkoxycarbonyl, (C$_1$–C$_4$)alkanoyloxy and di(C$_1$–C$_4$)alkylamino having independently the stated number of carbon atoms in each alkyl group; or when two adjacent positions on a phenyl ring are substituted with alkoxy groups, these groups may be joined to form a 5 or 6 membered dioxolano or dioxano heterocyclic ring;

R$^a$ is H, (C$_1$–C$_4$)alkyl, (C$_2$–C$_4$)alkenyl, (C$_1$–C$_4$)alkoxy, halo, halo(C$_1$–C$_4$)alkyl, halo(C$_1$–C$_4$)alkoxy, (C$_1$–C$_2$)alkoxy(C$_1$–C$_2$)alkyl, cyclopropyl or cyclopropyl substituted with 1–4 of the same or different halo or (C$_1$–C$_4$)alkyl, cyclopropyl(C$_1$–C$_2$)alkyl or cyclopropyl(C$_1$–C$_2$)alkyl substituted on the cyclopropyl ring with 1–4 of the same or different halo or (C$_1$–C$_4$)alkyl;

Z forms a 5-membered ring together with the carbon atoms to which it is attached and is selected from the group consisting of CR$^b$R$^c$—S(O)$_n$—NR$^d$, CR$^b$R$^c$—CR$^b$R$^c$—S(O)$_n$ wherein n is 1 or 2, CR$^b$R$^c$—CR$^b$R$^c$—NR$^d$, CR$^b$R$^c$—NR$^d$—O, CR$^b$R$^c$—NR$^d$—S(O)$_n$, CR$^b$=CR$^c$—S(O)$_n$ wherein n is 1 or 2, CR$^b$=CR$^c$—NR$^d$, CR$^b$=N—NR$^d$, CR$^b$=N—O, CR$^b$=N—CR$^b$R$_c$, CR$^b$=N—S(O)$_n$, CR$^b$R$^c$—NR$^d$—CR$^b$R$^c$, CR$^b$R$^c$—O—NR$^d$, CR$^b$R$^c$—S(O)$_n$—NR$^d$, S—CR$^b$R$^c$—O, S—CR$^b$R$^c$—S, S—CR$^b$R$^c$—NR$^d$, NR$^d$—CR$^b$R$^c$—O, O—CR$^b$R$^c$—S, O—CR$^b$R$^c$—NR$^d$, NR$^d$—CR$^b$R$^c$—S, NR$^d$—CR$^b$R$^c$—NR$^e$, N=CR$^b$—O,  N=CR$^b$—NR$^d$, CR$^b$R$^c$—N=N, NR$^d$—NR$^e$—S(O)$_n$, CR$^b$R$^c$—S(O)$_n$—CR$^b$R$^c$ wherein n is 1 or 2, CR$^b$=CR$^c$—CR$^b$R$^c$, N=CR$^d$—CR$^f$R$^g$, N=N—O, CR$^b$R$^c$—S—S, CR$^b$R$^c$—NR$^d$—NR$^e$, S(O)$_m$—O—CR$^b$R$^c$, NR$^d$—S(O)$_m$—S, NR$^d$—S(O)$_m$—O, NR$^d$—N=N, CR$^b$R$^c$—S(O)$_m$—O and NR$^d$—S(O)$_m$—NR$^e$ wherein R$^b$ and R$^c$ are each independently H, (C$_1$–C$_4$)alkyl, halo or together with the carbon to which they are attached form carbonyl or methylene, R$^d$ and R$^e$ are each independently H or (C$_1$–C$_4$)alkyl, R$^f$ and R$^g$ are each independently (C$_1$–C$_4$)alkyl, m is 1 or 2 and n is 0, 1 or 2.

3. An insecticidal compound having the formula

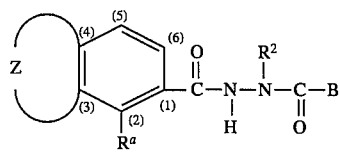

wherein

R$^2$ is a branched (C$_3$–C$_8$)alkyl;

B is phenyl or phenyl substituted with one to three of the same or different substituents selected from the group consisting of halo, (C$_1$–C$_2$)alkyl, (C$_1$–C$_2$)alkoxy, halo(C$_1$–C$_2$)alkyl, halo(C$_1$–C$_2$)alkoxy, (C$_1$–C$_2$)alkoxy(C$_1$–C$_2$)alkyl or when two adjacent positions on a phenyl ring are substituted with alkoxy groups, these groups may be joined to form a 5 or 6 membered dioxolano or dioxano heterocyclic ring;

R$^a$ is H, (C$_1$–C$_2$)alkyl, (C$_2$–C$_4$)alkenyl, (C$_1$–C$_2$)alkoxy, chloro, fluoro, chloro or polychloro(C$_1$–C$_2$)alkyl, fluoro or polyfluoro(C$_1$–C$_2$)alkyl, chloro or polychloro(C$_1$–C$_2$)alkoxy, fluoro or polyfluoro(C$_1$–C$_2$)alkoxy, (C$_1$–C$_2$)alkoxy(C$_1$–C$_2$)alkyl, cyclopropyl or cyclopropyl substituted with 1–4 of the same or different chloro, fluoro or (C$_1$–C$_2$)alkyl, cyclopropyl(C$_1$–C$_2$)alkyl or cyclopropyl(C$_1$–C$_2$)alkyl substituted on the cyclopropyl ring with 1–4 of the same or different chloro, fluoro or (C$_1$–C$_2$)alkyl;

Z forms a 5-membered ring together with the carbon atom (3) and (4) of the substituted phenyl ring to which it is attached and is selected from the group consisting of NH—S—CR$^b$R$^c$, NH—CR$^b$R$^c$—CR$^b$R$^c$, O—NH—CR$^b$R$^c$, S—NH—CR$^b$R$^c$, NH—CR$^b$=CR$^c$, NH—N=CR$^b$, O—N=CR$^b$, CR$^b$R$^c$—N=CR$^b$, S—N=CR$^b$, CR$^b$R$^c$—NH—CR$^b$R$^c$, NH—O—CR$^b$R$^c$, NH—S—CR$^b$R$^c$, O—CR$^b$R$^c$—S, S—CR$^b$R$^c$—S, NH—CR$^b$R$^c$—S, O—CR$^b$R$_c$—NH, S—CR$^b$R$^c$—O, NH—CR$^b$R$^c$—O, S—CR$^b$R$^c$—NH, NH—CR$^b$R$^c$—NH, O—CR$^b$=N, NH—CR$^b$=N, N=N—CR$^b$R$^c$, S—NH—NH, CR$^b$=CR$^c$—CR$^b$R$^c$, CR$^b$R$^c$—CR$^b$=CR$^c$, N=CR$^b$—CR$^f$R$^g$, N=N—O, and N=N—NH wherein R$^b$ and R$^c$ are each independently H, (C$_1$–C$_2$)alkyl, fluoro, chloro or together with the carbon to which they are attached form carbonyl or methylene, R$^f$ and R$^g$ are each independently (C$_1$–C$_2$)alkyl, and wherein the first atom of the Z-link is attached to carbon atom (3) of the phenyl ring and the last atom of the Z-link is attached to carbon atom (4) of the phenyl ring.

4. The compound of claim 3 wherein $R^2$ is tert-butyl, 1,1-dimethylpentyl or 1,1,3,3-tetramethylbutyl;

B is phenyl, 3,5-dimethylphenyl, 3-methylphenyl, 3-chlorophenyl, 3-fluorophenyl, 3,5-dichlorophenyl, 3,5-difluorophenyl, 3-chloro-5-methylphenyl or 3-fluoro-5-methylphenyl;

$R^a$ is H, $(C_1-C_2)$alkyl, vinyl, $(C_1-C_2)$alkoxy, chloro, fluoro, polychloro$(C_1-C_2)$alkyl, polyfluoro$(C_1-C_2)$alkyl, polyfluoro$(C_1-C_2)$alkoxy, methoxymethyl, cyclopropyl or cyclopropyl substituted with 1–4 of the same or different fluoro or $(C_1-C_2)$alkyl, cyclopropyl$(C_1-C_2)$alkyl or cyclopropyl$(C_1-C_2)$alkyl substituted on the cyclopropyl ring with 1–4 of the same or different fluoro or $(C_1-C_2)$alkyl;

Z forms a 5-membered ring together with the carbon atom (3) and (4) of the substituted phenyl ring to which it is attached and is selected from the group consisting of NH—$CR^bR^c$—$CR^bR^c$, $CR^b$=$CR^c$—$CR^bR^c$, $CR^bR^c$—$CR^b$=$CR^c$, N=$CR^b$—$CR^fR^g$ and NH—$CR^b$=$CR^c$, wherein $R^b$ and $R^c$ are each independently H, $(C_1-C_2)$alkyl, fluoro, chloro or together with the carbon to which they are attached form carbonyl or methylene, $R^f$ and $R^g$ are each independently $(C_1-C_2)$alkyl, and wherein the first atom of the Z-link is attached to carbon atom (3) of the phenyl ring and the last atom of the Z-link is attached to carbon atom (4) of the phenyl ring.

5. The compound of claim 4 wherein $R^2$ is tert-butyl;

B is 3,5-dimethylphenyl;

$R^a$ is H, methyl, ethyl or vinyl;

Z forms a 5-membered ring together with the carbon atom (3) and (4) of the substituted phenyl ring to which it is attached and is NH—$CR^bR^c$—$CR^bR^c$ wherein $R^b$ and $R^c$ are each independently H, methyl, ethyl, fluoro, or together with the carbon to which they are attached form carbonyl and wherein the first atom of the Z-link is attached to carbon atom (3) of the phenyl ring and the last atom of the Z-link is attached to carbon atom (4) of the phenyl ring.

6. An insecticidal composition for controlling insects which comprises an agronomically acceptable carrier and an insecticidally effective amount of one or more compounds of claim 1.

7. An insecticidal composition for controlling insects which comprises an agronomically acceptable carrier and an insecticidally effective amount of one or more compounds of claim 3.

8. A method of controlling insects comprising contacting the insects with an insecticidally effective amount of one or more compounds of claim 1.

9. A method of controlling insects comprising contacting the insects with an insecticidally effective amount of one or more compounds of claim 3.

* * * * *